United States Patent
Grostefon et al.

(10) Patent No.: US 10,322,003 B2
(45) Date of Patent: Jun. 18, 2019

(54) MODULAR TAPER SEAL AND METHOD FOR ORTHOPAEDIC PROSTHETIC HIP ASSEMBLY

(71) Applicant: DEPUY IRELAND UNLIMITED COMPANY, County Cork (IE)

(72) Inventors: Justin D. Grostefon, Columbia City, IN (US); Jeffrey A. McAnelly, Columbia City, IN (US)

(73) Assignee: DEPUY IRELAND UNLIMITED COMPANY, Ringaskiddy, County Cork (IE)

( * ) Notice: Subject to any disclaimer, the term of this patent is extended or adjusted under 35 U.S.C. 154(b) by 0 days.

(21) Appl. No.: 15/643,254

(22) Filed: Jul. 6, 2017

(65) Prior Publication Data

US 2017/0304062 A1    Oct. 26, 2017

Related U.S. Application Data

(63) Continuation of application No. 14/755,419, filed on Jun. 30, 2015, now Pat. No. 9,724,201.

(51) Int. Cl.
*A61F 2/36* (2006.01)
*A61F 2/30* (2006.01)

(52) U.S. Cl.
CPC .............. *A61F 2/3609* (2013.01); *A61F 2/36* (2013.01); *A61F 2002/30331* (2013.01); *A61F 2002/30332* (2013.01); *A61F 2002/30589* (2013.01); *A61F 2002/365* (2013.01); *A61F 2002/3625* (2013.01); *A61F 2250/0069* (2013.01)

(58) Field of Classification Search
CPC .... A61F 2/36; A61F 2/3607; A61F 2002/365; A61F 2002/3654; A61F 2002/3652; A61F 2002/30069; A61F 2002/30474; A61F 2002/3611
See application file for complete search history.

(56) References Cited

U.S. PATENT DOCUMENTS

| | | |
|---|---|---|
| 3,707,006 A | 12/1972 | Bokros et al. |
| 3,801,989 A | 4/1974 | McKee |
| 3,818,514 A | 6/1974 | Clark |
| 4,714,477 A | 12/1987 | Fichera et al. |
| 4,993,410 A | 2/1991 | Kimsey |
| 5,133,765 A | 7/1992 | Cuilleron |
| 5,147,366 A | 9/1992 | Arroyo et al. |

(Continued)

FOREIGN PATENT DOCUMENTS

| | | |
|---|---|---|
| CN | 2580920 Y | 10/2003 |
| CN | 101883540 A | 11/2010 |

(Continued)

OTHER PUBLICATIONS

International Search Report and Written Opinion, International Application No. PCT/US2016/032827, dated Aug. 5, 2016, 6 pages.

*Primary Examiner* — Brian A Dukert
(74) *Attorney, Agent, or Firm* — Barnes & Thornburg LLP

(57) ABSTRACT

An orthopedic prosthetic hip assembly and method for use during performance of a hip replacement procedure. The assembly includes a femoral stem component having a tapered trunnion and a femoral head component having a tapered bore. Upon insertion of the tapered trunnion into the tapered bore, a taper lock is formed and a seal provides a fluid-tight closure.

9 Claims, 4 Drawing Sheets

(56) References Cited

U.S. PATENT DOCUMENTS

| | | |
|---|---|---|
| 5,156,626 A | 10/1992 | Broderick et al. |
| 5,405,394 A | 4/1995 | Davidson |
| 5,425,779 A | 6/1995 | Schlosser et al. |
| 5,569,263 A | 10/1996 | Hein et al. |
| 5,674,225 A | 10/1997 | Mueller |
| 5,735,905 A | 4/1998 | Parr |
| 5,865,850 A * | 2/1999 | Matthews ............ A61F 2/3609 623/22.43 |
| 5,885,295 A | 3/1999 | McDaniel et al. |
| 5,888,211 A | 3/1999 | Sanders |
| 6,110,179 A | 8/2000 | Flivik et al. |
| 6,284,002 B1 | 9/2001 | Sotereanos |
| 6,344,060 B1 | 2/2002 | Schmotzer et al. |
| 6,585,771 B1 | 7/2003 | Buttermilch et al. |
| 7,179,297 B2 | 2/2007 | McLean |
| 7,192,449 B1 | 3/2007 | McQueen et al. |
| 8,840,676 B2 | 9/2014 | Belew et al. |
| 8,858,645 B2 | 10/2014 | Grostefon et al. |
| 9,615,927 B2 | 4/2017 | Huff et al. |
| 9,724,201 B2 | 8/2017 | Grostefon et al. |
| 2002/0052661 A1 | 5/2002 | Spotorno et al. |
| 2002/0193882 A1 | 12/2002 | Koller |
| 2004/0117029 A1 | 6/2004 | Lewis et al. |
| 2004/0199257 A1 | 10/2004 | Dooney |
| 2005/0143828 A1 | 6/2005 | Collins et al. |
| 2007/0100464 A1 | 5/2007 | Meulink |
| 2007/0250175 A1 | 10/2007 | Meridew et al. |
| 2010/0241239 A1 | 9/2010 | Smith |
| 2011/0247229 A1 | 10/2011 | Anapliotis et al. |
| 2012/0185059 A1 | 7/2012 | Vankoski et al. |
| 2012/0319332 A1 | 12/2012 | Mcminn |
| 2013/0204389 A1 | 8/2013 | Kumar et al. |
| 2013/0245775 A1 | 9/2013 | Metcalfe |
| 2013/0325139 A1 | 12/2013 | Steiner et al. |

FOREIGN PATENT DOCUMENTS

| | | |
|---|---|---|
| CN | 102458311 A | 5/2012 |
| DE | 10335442 A1 | 2/2005 |
| DE | 102008030260 A1 | 12/2009 |
| EP | 207873 A1 | 1/1987 |
| EP | 342014 A1 | 11/1989 |
| EP | 0663194 A1 | 7/1995 |
| EP | 807426 A2 | 11/1997 |
| EP | 1293179 A1 | 3/2003 |
| EP | 1825834 A1 | 8/2007 |
| EP | 2198808 A1 | 6/2010 |
| EP | 2574310 A2 | 4/2013 |
| FR | 1481424 A | 5/1967 |
| FR | 2105998 A5 | 4/1972 |
| GB | 1485295 A | 9/1977 |
| GB | 2042897 A | 10/1980 |
| GB | 2152385 A | 8/1985 |
| JP | 6007386 A | 1/1985 |
| JP | 11155890 A | 6/1999 |
| JP | 3172112 B2 | 6/2001 |
| JP | 2002345858 A | 12/2002 |
| JP | 2003175061 A | 6/2003 |
| JP | 4051950 B2 | 2/2008 |
| RU | 2309706 C2 | 11/2007 |
| WO | 1995022944 A1 | 8/1995 |
| WO | 2008117056 A1 | 10/2008 |
| WO | 2009106867 A1 | 9/2009 |
| WO | 2010129880 A2 | 11/2010 |
| WO | 2012035294 A2 | 3/2012 |
| WO | 2017053183 A1 | 3/2017 |

* cited by examiner

MODULAR TAPER SEAL AND METHOD FOR ORTHOPAEDIC PROSTHETIC HIP ASSEMBLY

This application claims priority under 35 U.S.C. § 120 to U.S. patent application Ser. No. 14/755,419, which was filed on Jun. 30, 2015 and is expressly incorporated herein by reference.

TECHNICAL FIELD

The present disclosure relates generally to an orthopaedic prosthetic assembly, and more particularly to an orthopaedic prosthetic hip assembly.

BACKGROUND

During the lifetime of a patient, it may be necessary to perform a joint replacement procedure on the patient as a result of, for example, disease or trauma. The joint replacement procedure may involve the use of a prosthetic assembly which is implanted into one of the patient's bones. In the case of a hip replacement procedure, a prosthetic hip assembly is implanted into the patient's hip joint. Such a prosthetic hip assembly typically includes a spherically-shaped head component which bears against the patient's natural or prosthetic acetabulum, along with an femoral stem component which is implanted in the patient's femur. In some designs, a proximal end of the femoral stem component is inserted into the femoral head component to couple the components to each other.

SUMMARY

According to one aspect of the disclosure, an orthopaedic prosthetic hip assembly includes a stem component configured to be received in a proximal end of a patient's surgically-prepared femur. The stem component includes a neck having a tapered trunnion and an elongated body extending distally from the neck. The assembly includes a femoral head component configured to engage a surgically-prepared acetabulum or a prosthetic acetabular cup. The femoral head component has a distal opening, a tapered bore extending inwardly from the distal opening to define an aperture sized to receive a proximal end of the stem component, and an annular slot defined in the tapered bore. The assembly includes a compressible seal is positioned in the annular slot of the femoral head component. The femoral head component is secured to the stem component via a taper lock formed between the tapered bore of the femoral head component and the tapered trunnion of the stem component. The compressible seal engages the tapered trunnion of the stem component to prevent fluid from advancing toward a proximal end of the aperture.

In some embodiments, the tapered trunnion of the stem component extends from a proximal end of the neck to a trunnion end surface, and the compressible seal is positioned between the trunnion end surface and the proximal end of the neck.

In some embodiments, the compressible seal is positioned close to the proximal end of the neck.

In some embodiments, the annular slot includes the distal opening.

In some embodiments, the neck includes an annular flange positioned adjacent to the tapered trunnion, and the compressible seal is engaged with the annular flange.

In some embodiments, the compressible seal is an O-ring. In some embodiments, the O-ring is formed from silicone. In some embodiments, the femoral head component includes a semi-spherical outer surface.

In some embodiments, the elongated body extends to a distal tip.

In another aspect, an orthopaedic prosthetic hip assembly, includes a stem component configured to be received in a proximal end of a patient's surgically-prepared femur. The stem component includes a neck including a tapered trunnion and an annular flange, and an elongated body extending distally from the neck. The assembly includes a femoral head component configured to engage a surgically-prepared acetabulum or a prosthetic acetabular cup. The femoral head component has a distal opening and an inner bore extending inwardly from the distal opening. The inner bore includes a first section that defines an annular slot and a tapered second section that defines an aperture extending inwardly from the annular slot. The assembly includes a compressible seal configured to be received in the annular slot of the femoral head component. The femoral head component is configured to be secured to the stem component via a taper lock formed between the tapered second section of the inner bore of the femoral head component and the tapered trunnion of the stem component. The flange of the stem component is configured to engage the compressible seal to prevent fluid from advancing into the aperture when the femoral head component is secured to the stem component.

In some embodiments, the neck includes an annular groove that is defined adjacent to the annular flange, the annular groove being sized to receive the compressible seal.

In some embodiments, the inner bore of the femoral head component further defines a seal surface connecting the first section and the tapered second section such that the compressible seal is positioned between the flange of the stem component and the seal surface when the femoral head component is secured to the stem component.

In some embodiments, the compressible seal is an O-ring. In some embodiments, the O-ring is formed from silicone. In some embodiments, the femoral head component includes a semi-spherical outer surface. In some embodiments, the elongated body extends to a distal tip.

BRIEF DESCRIPTION OF THE DRAWINGS

The detailed description particularly refers to the following figures, in which.

DETAILED DESCRIPTION OF THE DRAWINGS

Figure 1:
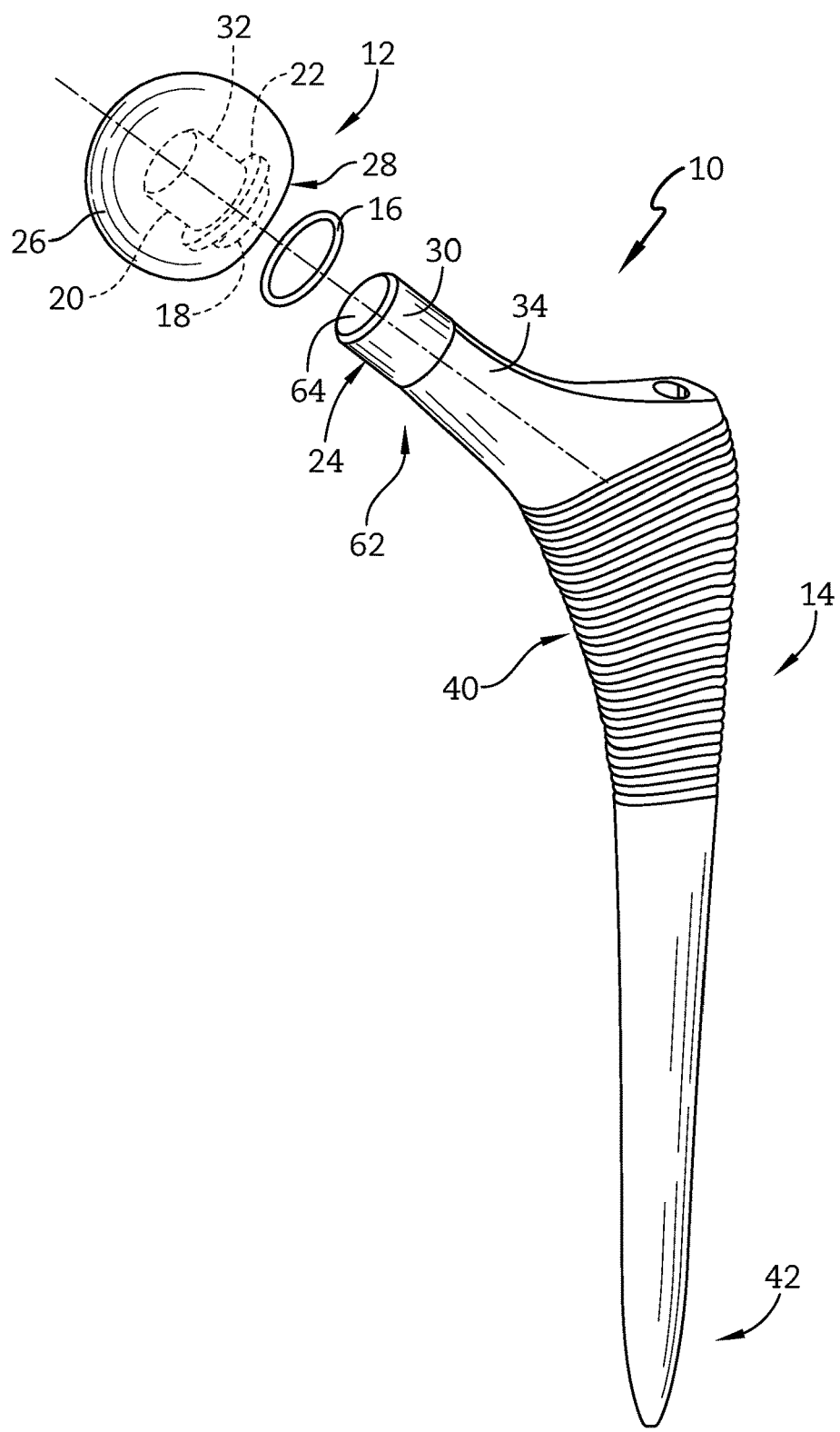
FIG. 1 is an exploded perspective view of an orthopaedic prosthetic hip assembly including a femoral stem component, a femoral head component, and a compressible seal.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, there is shown an orthopaedic prosthetic hip assembly 10 for use during performance of a hip replacement procedure. The orthopaedic prosthetic hip assembly 10 includes a femoral head component 12, a femoral stem component 14, and a compressible seal 16. The femoral head component 12 is configured to receive the femoral stem component 14 to couple the components 12, 14 to each other. When the femoral stem component 14 is received within the femoral head component 12, the compressible seal forms a fluid-tight closure to prevent ingress of material into the femoral head component 12, as described in greater detail below.

During hip joint replacement procedure, the femoral stem component 14 is implanted partially into the patient's femur and extends outwardly for connection with the femoral head component 12. The femoral stem component 14 has a tapered trunnion 24 extending in the proximal direction for connection with the femoral head component 12. The femoral head component 12 includes a tapered bore 20 configured to receive the tapered trunnion 24 of the femoral stem component 14. The tapered trunnion 24 of the femoral stem component 14 is configured to be seated within the tapered bore 20 to form a taper lock by mating between similarly tapered surfaces of each component 12, 14.

The tapered bore 20 of the femoral head component 12 includes an annular slot 22 that is configured to receive the compressible seal 16. When the femoral stem component 14 is inserted into the femoral head component 12 to form a taper lock, the compressible seal 16 is compressed by and bears against each of the femoral head component 12 and the femoral stem component 14 forming a fluid-tight closure that prevents ingress of foreign matter onto the taper lock of the femoral components 12,14.

In the illustrative embodiment shown in FIG. 1, the femoral stem component 14 includes a body 40 having a distal end 42 configured for implantation into a patient's femur. The femoral stem component 14 includes a neck 34 extending proximally from the body 40. The neck 34 has a proximal end 62 from which the tapered trunnion 24 proximally extends to a trunnion end surface 64. The trunnion 24 has a tapered outer surface 30 including a trunnion sealing surface 46, which is a portion of the tapered outer surface 30 in contact with the compressible seal 16 when the taper lock is formed. The trunnion 24 is tapered such that a diameter of the tapered outer surface 30 decreases along the direction of extension of the trunnion 24 from the neck 34 to the trunnion end surface 64. The taper angle of at least a portion of the tapered trunnion 24 is configured to be complimentary to a taper angle of at least a portion of the tapered bore 20 of the femoral head component 12 to form a taper lock when the femoral stem component 14 is inserted into the femoral head component 12. The trunnion sealing surface 46 is illustratively positioned distal to the portion of the tapered trunnion 24, which has a taper complimentary to the taper of the tapered bore 20 to form the taper lock.

The femoral head component 12 has semi-spherical outer surface 26 on a proximal end thereof for contact with the patient's natural or prosthetic acetabulum. The femoral head component 12 includes a flat distal surface 28 having a distal opening 18 defined therein. The tapered bore 20 extends proximally from the distal opening 18 and is defined by a tapered inner surface 32. The tapered bore 20 is tapered such that a diameter of the tapered inner surface 32 decreases along the direction of the extension of the tapered bore 20 from the distal opening 18. The taper angle of at least a portion of the tapered bore 20 is configured to be complimentary to the taper angle of at least a portion of the tapered outer surface 30 of the trunnion 24 such that at least a portion of the outer surface 30 is in contact with at least a portion of the tapered inner surface 32 when the trunnion 24 is seated within the tapered bore 20 to form a taper lock. The tapered bore 20 has an annular slot 22 configured to receive the compressible seal 16 for contact with the trunnion sealing surface 46 upon formation of a taper lock. The annular slot is illustratively positioned distal to the portion of the tapered bore 20 which has a taper complimentary to the taper of the trunnion 24 to form the taper lock.

Figure 2:
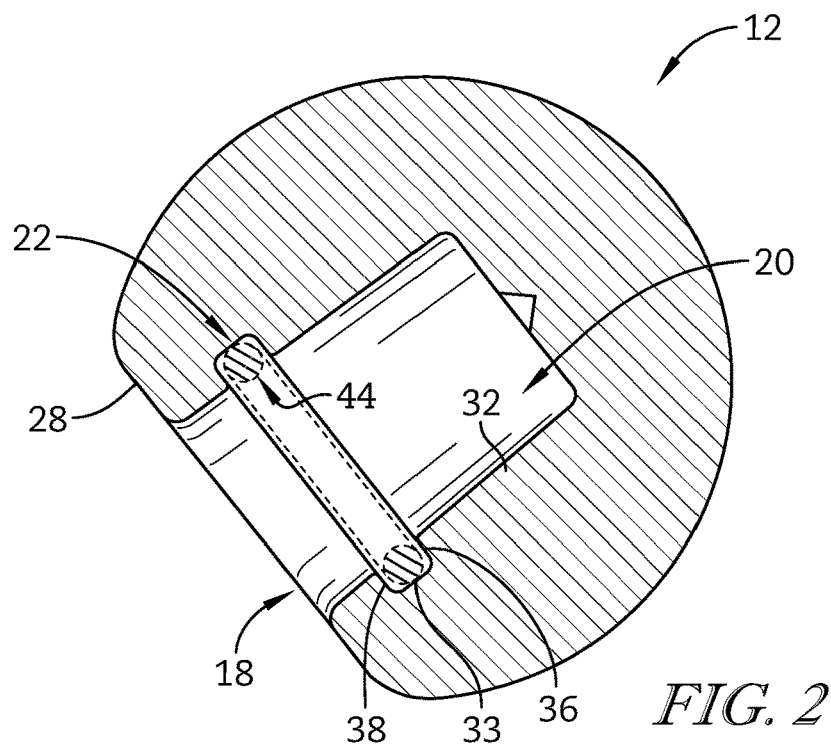
FIG. 2 is a cross-sectional view of the femoral head component of FIG. 1 taken along the line 2.2 in FIG. 1.

In the illustrative embodiment as shown in FIG. 2, the annular slot 22 is a groove formed in the tapered inner surface 32 and extends circumferentially around the tapered bore 20. The annular slot 22 illustratively has a square cross-section and is defined by an outer sealing surface 33, an annular proximal surface 36, and an annular distal surface 38 each extending circumferentially around the tapered bore 20. The proximal surface 36 and the distal surface 38 are positioned orthogonally to the outer sealing surface 33. The annular slot 22 is configured to receive the compressible seal 16 with a portion of an interior side 44 of the compressible seal 16 protruding radially inward into the tapered bore 20, as shown illustratively in FIG. 2.

The compressible seal 16 is an annular seal ring, as shown in the illustrative embodiment of FIG. 1. The compressible seal 16 is illustratively formed as an O-ring having a uniform circular cross-section as shown in FIG. 2, and defining an inner diameter and an outer diameter, the inner diameter defined by the interior side 44. The compressible seal 16 is configured to be received within the annular slot 22 of the femoral head component 12. A portion of the interior side 44 of the compressible seal 16 illustratively protrudes radially inward from the annular slot 22 through the tapered inner surface 32 into the tapered bore 20, as shown in FIG. 2. When unstressed, the compressible seal 16 illustratively defines an inner diameter smaller than an outer diameter defined by the trunnion sealing surface 46 of the trunnion 24.

The compressible seal 16 is illustratively formed of silicone to form fluid-tight sealing contact between the trunnion sealing surface 46 and the outer sealing surface 33 of the annular slot 22. In some embodiments, the compressible seal 16 may be formed of any suitable material for sealing and may have a cross-section having any shape to facilitate sealing between the trunnion sealing surface 46 and the femoral head component 12. For example, the compressible seal may have an ovular, square, or non-conventional cross-sectional shape.

Figure 3:
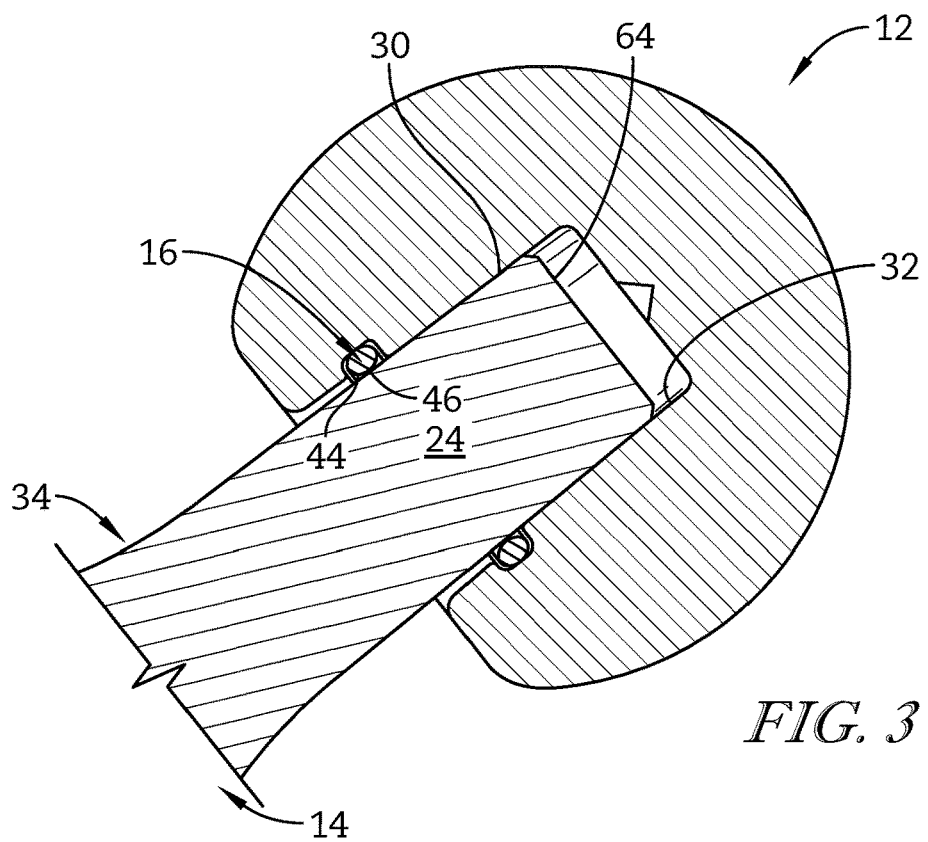
FIG. 3 is a cross-sectional view similar to FIG. 2 showing the femoral stem component secured to the the femoral head component and the compressible seal.

As shown in the illustrative embodiment of FIG. 3, when the trunnion 24 is inserted within the tapered bore 20 the complimentary portions of the tapered outer surface 30 of the tapered trunnion 24 and the tapered inner surface 32 defining the tapered bore 20 engage each other to form a taper lock. During the taper lock, the compressible seal 16 is positioned between the proximal end 62 of the neck 34 and the trunnion end surface 64. The interior side 44 of the compressible seal 16 contacts the trunnion sealing surface 46. The trunnion sealing surface 46 presses the interior side 44 of the compressible seal 16 radially outward such that the inner diameter of the compressible seal 16 is increased outwardly to equal that of the trunnion sealing surface 46. The compressible seal 16 is illustratively compressed between the trunnion sealing surface 46 and the outer sealing surface 33 to form a fluid-tight closure.

In the illustrative embodiment, the annular slot 22 has a square cross-sectional shape and the compressible seal 16 has a circular cross-sectional shape. The difference in these cross-sectional shapes permits expansion of the compressible seal's geometry into the unoccupied area within the annular slot 22 during assembly. Each of the illustrative annular slot 22 and compressible seal 16 have corresponding cross-sectional and diametric sizes. The particular sizes and shapes of each of the annular slot 22 and the compressible seal 16 thus coordinate to provide a fluid-tight closure between the trunnion 24 and the femoral head component 12. This fluid-tight closure prevents ingress of foreign material onto the tapered surfaces of the components 12, 14.

In some embodiments, the compressible seal 16 and the annular slot 22 may be sized such that upon formation of a taper lock, the inner diameter of the compressible seal 16 is increased outwardly to equal that of the trunnion sealing surface 46, but that the compressible seal 16 does not contact the outer sealing surface 33 of the annular slot 22. In some embodiments, the compressible seal 16 and the annular slot 22 may be configured such that upon formation of a taper lock, the compressible seal 16 may contact one or more of the proximal surface 36 and the distal surface 38. In some embodiments, the compressible seal 16 may be positioned at any point between the proximal end 62 of the neck 34 and the trunnion end surface 64 during taper lock.

Figure 4:
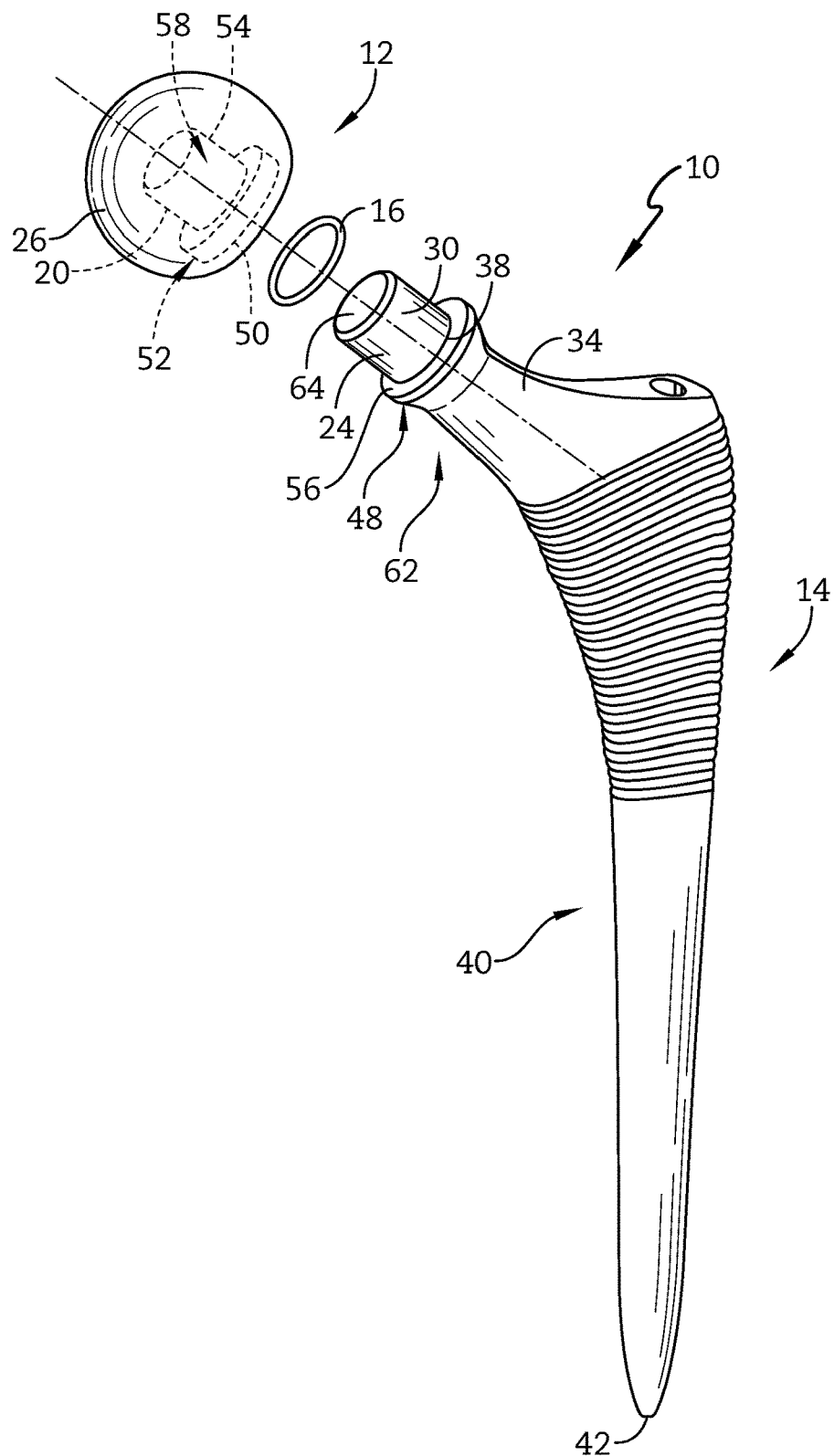
FIG. 4 is an exploded perspective view of another orthopaedic prosthetic hip assembly including a femoral stem component, a femoral head component, and a compressible seal.

In the illustrative embodiment as shown in FIG. 4, an othopaedic prosthetic hip assembly 10 includes a femoral head component 12, femoral stem component 14, and a compressible seal 16, similar to that shown in FIG. 1. Where aspects of features of the foregoing description remain largely unchanged from that of the description below, for convenience, the same numerals have been maintained throughout the illustrative figures. The orthopaedic prosthetic hip assembly 10 forms taper lock by inserting a tapered trunnion 24 of the femoral stem component 14 into the tapered bore 20 of the femoral head component 12. The femoral stem component 14 illustratively includes an annular flange 48 extending radially outward from the neck 34 adjacent to the tapered trunnion 24. The annular flange 48 includes an upper surface 56 located on a proximal side thereof.

Figure 5:
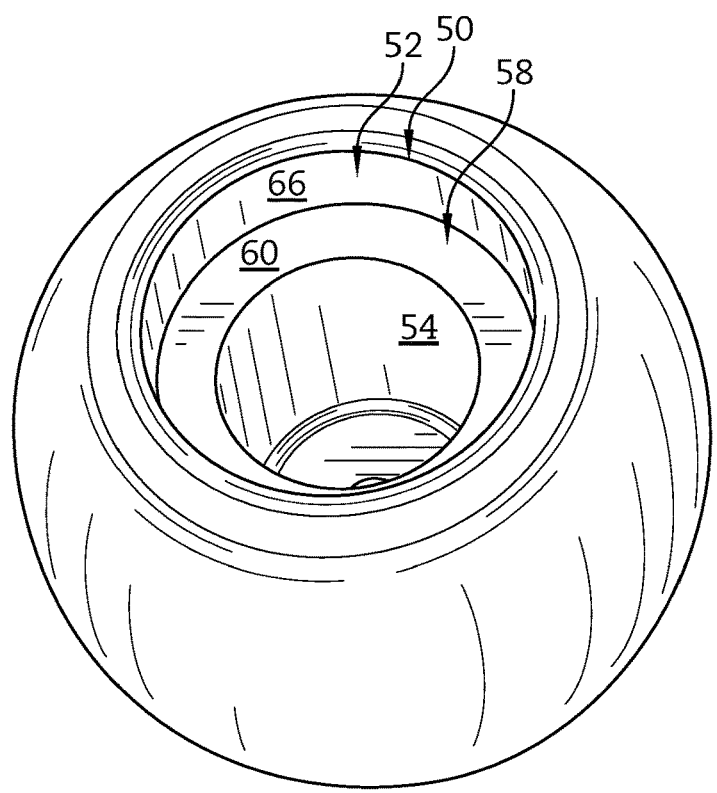
FIG. 5 is distal perspective view of the femoral head component of FIG. 4.

As shown in FIG. 5, the femoral head component 12 includes a distal opening 50 from which a tapered bore 58 proximally extends. The tapered bore 58 is defined at least partially by a tapered inner surface 54. The tapered inner surface 54 includes an annular slot 52 adjacent the distal opening 50. The annular slot 52 is defined by an outer sealing surface 66 and a proximal surface 60, the proximal surface 60 being orthogonal to the outer sealing surface 66. Each of the outer sealing surface 66 and the proximal surface 60 extend circumferentially around the annular slot 52. The annular slot 52 is configured to receive the compressible seal 16 and the annular flange 48 of the femoral stem component 14. The tapered inner surface 54 extends proximally from the proximal surface 60 of the annular slot 52 and is configured for receiving the tapered trunnion 24 to form a taper lock.

Figure 6:
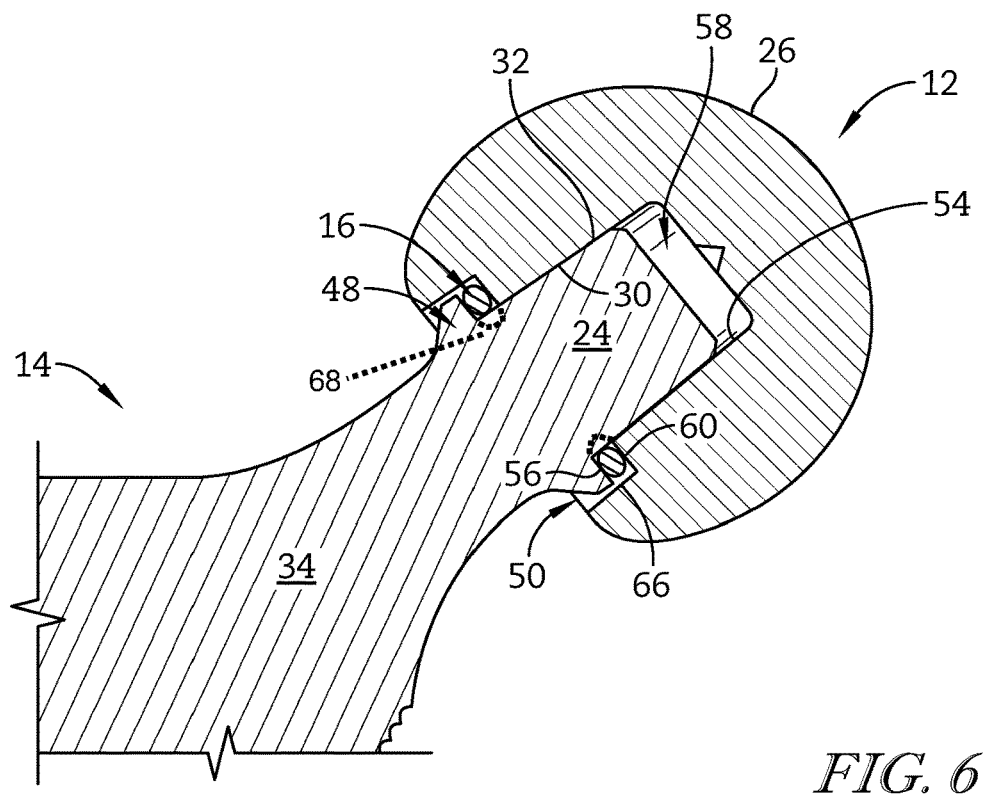
FIG. 6 is a cross-sectional view showing the femoral stem component secured to the femoral head component and the compressible seal.

In the illustrative embodiment as shown in FIG. 6, the compressible seal 16 is positioned around the tapered trunnion 24 adjacent to the annular flange 48. When the trunnion 24 is inserted into the tapered bore 58 of the femoral head component 12 and forms the taper lock, the compressible seal 16 is received within the annular slot 52. The compressible seal 16 is compressed between the proximal surface 60 of the annular slot 52 and the upper surface 56 of the annular flange 48 to form a fluid-tight closure preventing ingress of foreign material onto the taper lock.

The compressible seal 16, as illustrated in FIG. 6, is an annular ring defining an inner diameter equal to an outer diameter of the trunnion 24 adjacent to the annular flange 48. The compressible seal illustratively has a circular cross-section. In some embodiments, the trunnion 24, at an outer surface adjacent to the flange, may comprise a seal groove 68 (shown by the dotted line imaginary boundary in FIG. 6) extending circumferentially around the trunnion, the seal groove having a shape complimentary to the shape of the compressible seal 16 and being configured to receive the compressible seal 16. In some embodiments, the compressible seal 16 may have any cross-sectional shape, cross-sectional size, and or diametric size to provide fluid-tight sealing between the femoral components 12, 14 upon formation of the taper lock.

In some embodiments, the femoral stem component 14 and the femoral head component may be provided in a number of different size configurations in order to fit the needs of a given patient's anatomy. In particular, the geometry of the tapered bore 20, 58 of each of the femoral head components 12 may be identical, and the geometry of each of the tapered trunnion 24 of the differently sized femoral stem components 14 may be identical. Because the taper features of the femoral head components 12 and femoral stem components 14 are commonly sized across the range of component sizes, each of the differently-sized femoral head components 12 is compatible with each of the differently-sized femoral stem components 14.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. A method of assembling an orthopaedic prosthetic hip assembly, the method comprising:
   positioning a compressible seal in an annular slot of a femoral head component, the femoral head component being configured to engage a surgically-prepared acetabulum or a prosthetic acetabular cup, aligning a tapered trunnion of a femoral stem component with a distal opening of the femoral head component, advancing the tapered trunnion of the femoral stem component into the distal opening through a distal section of an inner bore of the femoral head component and into a tapered section of the inner bore that is defined by an inner surface of the femoral head component, engaging the tapered trunnion of the femoral stem component with the inner surface of the femoral head component to secure the femoral stem component to the femoral head component, and engaging a flange of the femoral stem component with the compressible seal, wherein the distal section of the inner bore includes the annular slot.

2. The method of claim 1, further comprising positioning the compressible seal in an annular groove defined in the femoral stem component.

3. The method of claim 1, wherein engaging the flange of the femoral stem component with the compressible seal includes positioning the compressible seal between a distal surface of the femoral head component and a proximal surface of the flange of the femoral stem component.

4. A method of assembling an orthopaedic prosthetic hip assembly, the method comprising:

positioning a compressible seal in an annular slot of a femoral head component, the annular slot extending circumferentially around an inner bore of the femoral head component, and the femoral head component being configured to engage a surgically-prepared acetabulum or a prosthetic acetabular cup, aligning a tapered trunnion of a femoral stem component with a distal opening of the femoral head component, advancing the tapered trunnion of the femoral stem component into the distal opening through a distal section of the inner bore of the femoral head component and into a tapered section of the inner bore that is defined by an inner surface of the femoral head component, and securing the compressible seal between the femoral stem component and the femoral head component to prevent fluid from advancing proximally along the tapered trunnion, wherein the distal section of the inner bore includes the annular slot, the annual slot extending from a circumferential opening defined in the inner surface of the femoral head component.

5. The method of claim 4, further comprising engaging the tapered trunnion of the femoral stem component with the inner surface of the femoral head component to secure the femoral stem component to the femoral head component.

6. The method of claim 4, wherein securing the compressible seal between the femoral stem component and the femoral head component includes positioning the compressible seal between a distal surface and a proximal surface of the femoral head component and a section of the tapered trunnion of the femoral stem component.

7. A method of assembling an orthopaedic prosthetic hip assembly, the method comprising:

positioning a compressible seal in an annular slot of a femoral head component, the femoral head component being configured to engage a surgically-prepared acetabulum or a prosthetic acetabular cup, aligning a tapered trunnion of a femoral stem component with a distal opening of the femoral head component, advancing the tapered trunnion of the femoral stem component into the distal opening through a distal section of an inner bore of the femoral head component and into a tapered section of the inner bore that is defined by an inner surface of the femoral head component, and securing the compressible seal between the femoral stem component and the femoral head component to prevent fluid from advancing proximally along the tapered trunnion, wherein the distal section of the inner bore includes the annular slot, and wherein securing the compressible seal between the femoral stem component and the femoral head component includes positioning the compressible seal between a distal surface of the femoral head component and a flange of the femoral stem component.

8. The method of claim 7, further comprising engaging the tapered trunnion of the femoral stem component with the inner surface of the femoral head component to secure the femoral stem component to the femoral head component.

9. The method of claim 7, wherein securing the compressible seal between the femoral stem component and the femoral head component includes positioning the compressible seal between a distal surface and a proximal surface of the femoral head component and a section of the tapered trunnion of the femoral stem component.

* * * * *